United States Patent [19]

Rogier

[11] 4,348,543

[45] Sep. 7, 1982

[54] CYCLOALIPHATIC ALCOHOLS

[75] Inventor: Edgar R. Rogier, Minnetonka, Minn.

[73] Assignee: Henkel Corporation, Minneapolis, Minn.

[21] Appl. No.: 233,793

[22] Filed: Feb. 12, 1981

[51] Int. Cl.$^3$ .................. C07C 35/18; C07C 35/14
[52] U.S. Cl. .................... 568/823; 568/825; 568/826; 568/827; 568/829; 568/831
[58] Field of Search ............ 568/823, 825, 831, 822, 568/826, 827, 834, 833, 829

[56] References Cited

U.S. PATENT DOCUMENTS

| | | | |
|---|---|---|---|
| 2,917,549 | 12/1959 | Hasek et al. | 568/831 |
| 4,038,326 | 7/1977 | Kuper | 568/826 |
| 4,216,343 | 8/1980 | Rogier | 568/853 |

FOREIGN PATENT DOCUMENTS 1043507  9/1966  Canada .................. 568/822

OTHER PUBLICATIONS

Adkins "J. Amer. Chem. Soc." vol. 54, (1932) p. 1138+.

*Primary Examiner*—Werren B. Lone
*Attorney, Agent, or Firm*—Forrest L. Collins; Patrick J. Span

[57] ABSTRACT

The present invention describes cycloaliphatic alcohols prepared via a Diels-Alder reaction.

10 Claims, No Drawings

CYCLOALIPHATIC ALCOHOLS

BACKGROUND OF THE INVENTION

1. Field of the Invention

This invention relates to the preparation of polyfunctional alcohols which may be utilized among other purposes for the preparation of polyurethanes.

2. Description of the Art Practices

It is known that polyfunctional cycloaliphatic acids may be prepared through a Diels-Alder reaction. Such materials are useful in the preparation of polyesters. However, the ester bond itself is subject to attack by a number of chemical agents. It has been found desirable by the present author to prepare a compound not subject to an ester attack by eliminating the carboxycyclic acid functionality of the resultant compound. The claimed compounds have the advantage of high flexibility when used in urethanes and in light stability when the compound is hydrogenated.

The author has also made considerable disclosures in the art in his earlier U.S. Pat. No. 4,216,343 dated Aug. 5, 1980 herein incorporated by reference.

Throughout the specification and claims, percentages and ratios are by weight and temperatures in degrees Celsius unless otherwise indicated.

SUMMARY OF THE INVENTION

The present invention claims a member selected from the group consisting of

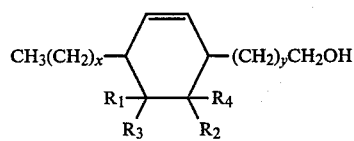

(I)

and

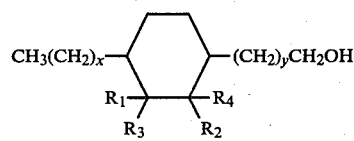

(II)

and mixtures thereof wherein $R_1$ and $R_2$ are selected from the group consisting of hydrogen and methyl and mixtures thereof with the provision that one such member must be hydrogen; and $R_3$ and $R_4$ are hydrogen or hydroxymethyl provided that at least one of $R_3$ and $R_4$ must be hydroxymethyl; and further that x is an integer of from 3 through 6 and y is an integer from 6 through 9 and that the sum x plus y is 12.

DETAILED DESCRIPTION OF THE INVENTION

As indicated previously, the novel compounds of the present invention may either contain a saturated or unsaturated bond within the six membered ring structure of the described compounds. This is particularly important in that should it be desired to promote ultraviolet stability, the bond within the ring structure may be hydrogenated or if a fire retardant property or some further derivatization is desired, the unsaturation may be left in the molecule thereby providing an active site.

The novel polyols of this invention which contain all primary alcohol groups can be prepared by reduction of acids or esters of structure (III) or (IV).

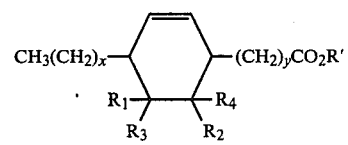

III

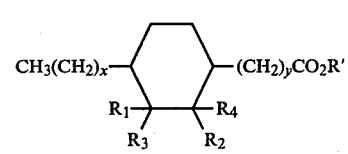

IV

In the above formulas of the acid or ester, $R_1$, $R_2$, x and y have the definitions previously set forth, preferably 4 or 5 for x and 7 or 8 for y; and $R_3$ and $R_4$ are hydrogen or $CO_2R'$ with the provision that if one of the radicals is hydrogen the other must be $CO_2R'$. $R'$ may be either hydrogen or an alkyl group containing preferably from 1 to 6 carbon atoms. Further unsaturation may be present in the linear portion of the molecule (III) if a material such as tung oil is employed.

The carbon-carbon double bonds of the above cyclohexane derivatives (III) can be saturated by catalytic hydrogenation using catalysts such as Raney nickel, supported nickels, palladium or platinum.

Either unsaturated esters (III) or saturated esters (IV) can be converted into saturated polyols (II) by hydrogenolysis using copper chromite catalysts such as those described by Adkins J. Amer. Chem. Soc. 54, 1138 (1932) or commercially available modifications of copper chromite catalysts.

If the unsaturated polyols (I) are desired, the ester groups of the unsaturated esters (III) can be hydrogenolyzed with the carbon-carbon double bonds being preserved by using chemical reducing agents such as sodium metal and alcohols (Bouveault-Blanc reductions) or $LiAlH_4$.

The acids and esters may be prepared from a variety of conjugated fatty acids or their derivatives and a dieneophile. This latter mentioned process is the Diels-Alder reaction as previously described. Basically, the Diels-Alder reaction is conducted after obtaining the methyl ester of a drying or semi-drying oil through methanolysis. Conveniently, the methyl ester may be obtained by methanolysis of tung oil. For the sake of simplicity, methanolysis is mentioned, however, any alcoholysis reaction may be employed.

Variations in the present invention allow the use of various unsaturated materials which are derived from the semi-drying oils such as those selected from the group consisting of soybean oil, tall oil, tung oil, linseed oil, safflower oil, sunflower oil and other similar materials.

Various unsaturated acids may be utilized herein as previously indicated including those conveniently having 18 carbon atoms such as 9, 12-octadecadienoic acid (linoleic acid); 9, 11-octadecadienoic acid, 10, 12-octadecadienoic acid; 9,12,15-octadecatrienoic acid, (linolenic acid); 6,9,12-octadecatrienoic acid; 9,11,13-octadecatrienoic acid (eleostearic acid); 10,12,14-octadecatrienoic acid and the other similar materials. It is also noted as previously stated that various derivatives of the fatty acids may be employed, particularly the alkyl esters and particularly those containing up to 8 carbon atoms. Most conveniently, however, the methyl ester is employed for reasons of convenience and expense. It is also noted that a particularly interesting variable in the present invention is to conjugate the double bonds of the fatty acids described above and such may be done by known techniques such as alkali conjugation. Conjugation by some method is necessary for the Diels-Alder reaction.

Dieneophiles which can be used in the preparation of III include acrylic acid, methacrylic acid, crotonoic acid, maleic acid, fumaric acid and the $C_1$ to $C_8$ esters of such acids. Maleic anhydride may also be employed.

The dieneophile and methyl ester of the drying oil together with a polymerization inhibitor such as para-methoxyphenol are charged into a reactor flushed with nitrogen and heated to a temperature of from about 110 to 180 degrees C for a substantial period of time. After the reaction is complete, any excess dieneophile is then removed and the unpurified unsaturated cycloaliphatic material is obtained.

Where the saturated material is required, the above product III can be reduced using a common hydrogenation catalyst. Most practically plantinum and palladium on carbon be utilized. The material as described above is then saturated by placing it in a reaction vessel with the 5 percent palladium on carbon catalyst and the reaction vessel is flushed with nitrogen followed by pressurization with hydrogen gas at from about 1 to about 500 atmospheres. The temperature is maintained during the hydrogenation at from about 20 to 150, preferably 55 to 135 degrees Celsius. The pressure during the hydrogenation reaction is conveniently maintained at from about 10 to about 200 atmospheres. The reaction time is simply that required to obtain as much degree of hydrogenation as is desired. Conveniently, this reaction may be conducted from about 3 to 8 hours.

Thereafter, the acid or ester is reacted utilizing hydrogen gas and copper chromite utilizing conditions for reduction of the acid or ester to the corresponding alcohols shown in the Summary.

It has been found that such a hydrogenolysis reaction with the copper chromite catalyst may be conducted at from about 240 degrees C. to about 300 degrees C., preferably from about 250 degrees C. to about 280 degrees C. The pressure for the hydrogenation reaction may be maintained at from about 200 to 500 atmospheres, preferably from about 220 to about 480 atmospheres.

The compounds of the present invention may be used to prepare urethanes and melamine coatings.

The following are illustrative examples of the present invention.

EXAMPLE I

The preparation of unsaturated 21 carbon dimethyl ester of tung oil (III) is conducted as follows:

Into a 70-gallon reaction vessel is placed 201 pounds of a methyl ester derived by methanolysis of tung oil, 59.7 pounds of methyl acrylate and 271 grams of p-methoxyphenol.

The reaction vessel is then flushed with nitrogen and then heated to about 145 degrees C. for a period of approximately 24 hours. The excess methyl acrylate is then removed by distillation at a temperature of approximately 100 degrees Celsius and reduced pressure.

Schematically, the above reaction is shown as follows:

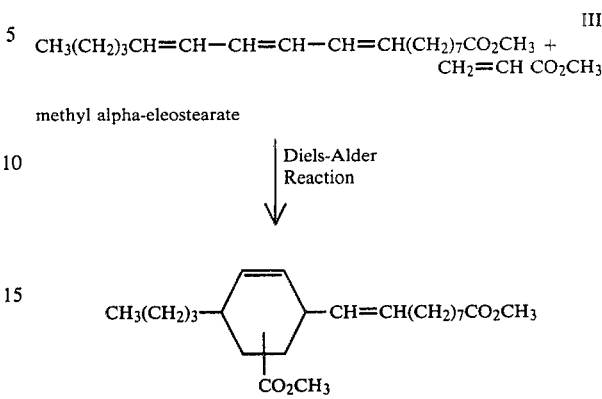

EXAMPLE II

A 70-gallon autoclave is charged with 217 pounds of the unsaturated dimethyl ester (III) and 4.4 pounds of 5 percent palladium on carbon. The reaction vessel is then flushed with nitrogen and pressurized with hydrogen to 7 atmospheres.

The temperature is maintained at 75-115 degrees during the hydrogenation of the unsaturation in the cyclohexene ring. The pressure utilized during the hydrogenation is from about 2 to 6 atmospheres.

After hydrogenation is complete (6.5 hours), the reaction vessel is flushed with nitrogen and discharged through a pressure filter to yield 214 pounds of the saturated dimethyl ester (IV).

Any noncyclic material may be removed by a fractional distillation. These materials are primarily those corresponding to the aliphatic acids employed. The final distilled product had a saponification equivalent weight equal to 193.

EXAMPLE III

Product obtained from Example II which has been distilled using a wiped film still to remove any noncyclic material is utilized in this and the succeeding examples. Into a 1 liter 316 SS Magne Drive autoclave is placed 500 grams of the saturated dimethyl ester (IV) and 50 grams of copper chromite catalyst obtained from the Harshaw Chemical Company. The autoclave is then purged with nitrogen and pressurized with hydrogen gas to 200 atmospheres.

The reaction vessel is then heated to 250 degrees C. where hydrogen uptake begins. The temperature is increased to 270 degrees and the pressure maintained at from about 208 to 250 atmospheres by hydrogen addition for 6½ hours. The reaction vessel is then cooled to about 200 degrees C. and any excess hydrogen and methanol is vented. The product is discharged through a pressure filter and obtained as a colorless liquid diol having a hydroxyl equivalent weight of approximately 176 (Compound II) where either $R_3$ or $R_4$ is hydroxymethyl and $R_1$, $R_2$ and either $R_3$ or $R_4$ are hydrogen and $x=3$ and $y=9$. Remarkably, the viscosity of the product obtained is quite low.

Additional runs are shown in Table 1.

TABLE I
PREPARATION OF 21 CARBON DIHYDRIC CYCLOALIPHATIC ALCOHOL THROUGH HYDROGENOLYSIS OF THE CORRESPONDING DIMETHYL ESTER USING COPPER CHROMITE CATALYST

| CHARGE | | | | | | |
|---|---|---|---|---|---|---|
| C-21 Di Me Ester (IV) (g) | g of Catalyst/ 100 g Me Ester | Time (hrs) | Temp[2] °C. | Pressure (Atmospheres) | Hydroxyl Eq. Wt. | Sap. # |
| 499.6 | 10.0 | 1.0 | 265 | 238 | 176 | 6.7 |
| | | 6.5 | 270–273 | 245 | | |
| 597.8 | 6.7 | 1.2 | RT→270 | 195 | 173 | 4.7 |
| | | 9.25 | 271 | 238 | | |
| 604.3 | 10.0 | 1.17 | RT→268 | 192 | | |
| | | 6.75 | 268–270 | 246–252 | 173 | 5.1 |

(IV) Hydrogenated Diels-Alder adduct of Methyl Eleostearate and Methyl Acrylate
[2]RT is room temperature.

EXAMPLE IV
PREPARATION OF TRIESTER[1]

Into a 5 liter Pyrex flask equipped with a reflux condenser and source of nitrogen purge is placed 1208 grams of the methyl esters of tung oil fatty acids (77 percent eleostearic acid) and 636 grams of dimethyl maleate. The reaction system is flushed with nitrogen and heated at 180 degrees C. for 24 hours.

The reaction product is combined with the product of a similar run starting with 301 grams of methyl tungate. The combined crude products after stripping of excess dimethyl maleate by distillation under reduced pressure weigh 2222 grams. Thin-film distillation of 2191 grams of this residue yielded the following fractions:

| Fract. No. | Pressure (torr) | Wt (g) | Saponification eq. wt. | % Triester* | VIII |
|---|---|---|---|---|---|
| 1 | 0.8–0.2 | 499 | | | |
| 2 | 0.4 | 694 | 181 | 98 | |
| 3 | 0.2–0.4 | 600 | 172 | 88 | |
| 4 | 0.4 | 92 | | 44 | |
| Residue | | 124 | | | |
| Trap condensate | | 123 | | | |

*Determined by Gas Chromatography. Sum of all isomer triesters.
[1]Triester Formula

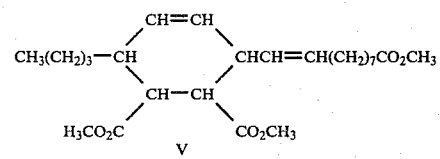

V

EXAMPLE V
HYDROGENOLYSIS OF TRIESTER

Into a 1 liter, 316 SS Magne-Drive autoclave is charged 497 grams of the triester V (Fract 2, above) and 50 grams of copper chromite catalyst (Cu-1910-P, Harshaw Chemical Co.). The autoclave is flushed with nitrogen, then charged with hydrogen to 200 atmospheres and heated to 270 degrees C. The reaction is maintained at 270 degrees C and 200–250 atmospheres pressure for 12 hours. The reaction is cooled, vented, flushed with nitrogen and filter under pressure. The filtered product weighed 315 grams after vacuum stripping and had hydroxyl equivalent weight of 286. The product contains the structure shown below.

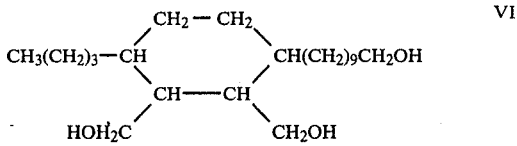

VI

EXAMPLE VI

The compounds of Example III are prepared into melamine coatings as shown below:

| Melamine Used: | Cymel 303 | Cymel 303 | Cymel 303 |
|---|---|---|---|
| Ratio of Diol (XXI) Melamine: | 70/30 | 40/60 | 60/40 |
| Cure Temperature: | 150° C. | 150° C. | 150° C. |
| Cure Time: | 30 min. | 30 min. | 30 min. |
| Pencil Hardness to Scratch: | HB - F | H - 2H | F - H |
| Impact: | | | |
| Forward: | 60 | 20 | 40 |
| | | 40 | 60 |
| Reverse: | 40 | 1 | 5 |
| | 60 | 2 | 10 |

The compositions herein are suitable for melamine curing agents, urethanes and similar products requiring hydroxyl functionality or hydroxyl with unsaturation. The esters are, of course, useful as the precursor to the various alcohols described herein.

What is claimed is:

1. A cycloaliphatic alcohol which is a member selected from the group consisting of

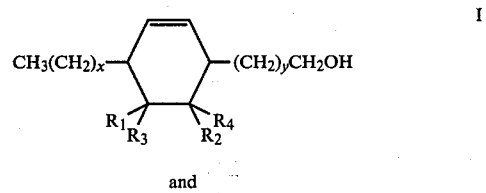

I and

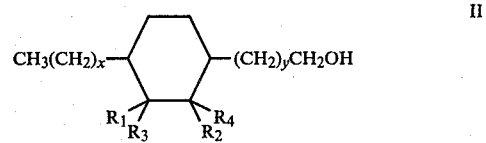

II and mixtures thereof wherein $R_1$ and $R_2$ are selected from the group consisting of hydrogen and methyl and mixtures thereof with the provision that one such member must be hydrogen; and $R_3$ and $R_4$ are hydrogen or hydroxymethyl provided that at least one but not both of $R_3$ and $R_4$ must be hydroxymethyl; and further that x is an integer of from 3 through 6 and y is an integer from 6 through 9 and that the sum x plus y is 12.

2. The compound of claim 1 wherein $R_1$ and $R_2$ are both hydrogen.

3. The compound of claim 1 wherein $R_3$ is hydroxymethyl.

4. The compound of claim 1 wherein $R_4$ is hydroxymethyl.

5. The compound of claim 1 wherein $R_3$ and $R_4$ are both hydroxymethyl.

6. The compound of claim 1 where x is 4 or 5 and y is 7 or 8.

7. The compound of claim 1 wherein $R_1$ and $R_2$ are both H and either $R_3$ or $R_4$ is $CH_2OH$.

8. The compounds of claim 1 wherein $R_1$ and $R_2$ are both H and $R_3$ and $R_4$ are both $CH_2OH$.

9. A cycloaliphatic alcohol which is a member selected from the group consisting of:

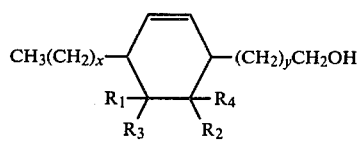
(I)

and

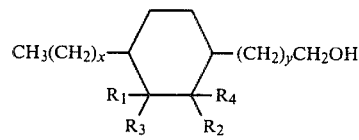
(II)

and mixtures thereof wherein $R_1$ and $R_2$ are selected from the group consisting of hydrogen and methyl and mixtures thereof with the provision that one such member must be hydrogen; and $R_3$ and $R_4$ are hydroxymethyl; and further that x is an integer of from 3 through 6 and y is an integer from 6 through 9 and that the sum x plus y is 12.

10. The compound of claim 9 wherein $R_1$ and $R_2$ are both hydrogen.

* * * * *